(12) United States Patent
Dasbach

(10) Patent No.: US 10,173,012 B2
(45) Date of Patent: Jan. 8, 2019

(54) MEDICAMENT DELIVERY DEVICE WITH TWO DRIVE SPRINGS

(71) Applicant: Sanofi-Aventis Deutschland GMBH, Frankfurt am Main (DE)

(72) Inventor: Uwe Dasbach, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 15/026,680

(22) PCT Filed: Oct. 13, 2014

(86) PCT No.: PCT/EP2014/071906
§ 371 (c)(1),
(2) Date: Apr. 1, 2016

(87) PCT Pub. No.: WO2015/055588
PCT Pub. Date: Apr. 23, 2015

(65) Prior Publication Data
US 2016/0243310 A1    Aug. 25, 2016

(51) Int. Cl.
*A61M 5/00* (2006.01)
*A61M 5/315* (2006.01)
*A61M 5/20* (2006.01)
*A61M 5/32* (2006.01)

(52) U.S. Cl.
CPC ...... *A61M 5/31513* (2013.01); *A61M 5/2033* (2013.01); *A61M 5/3158* (2013.01); *A61M 5/3204* (2013.01); *A61M 5/3157* (2013.01); *A61M 5/31511* (2013.01); *A61M 5/31568* (2013.01); *A61M 2005/31518* (2013.01)

(58) Field of Classification Search
CPC ...... A61M 2005/31518; A61M 5/2033; A61M 5/31511; A61M 5/31513; A61M 5/3158; A61M 5/3204
See application file for complete search history.

(56) References Cited

U.S. PATENT DOCUMENTS 3,749,084 A * 7/1973 Cucchiara .......... A61B 5/02755
                                                    600/575
2013/0060231 A1* 3/2013 Adlon ................ A61M 5/3234
                                                    604/506

(Continued)

FOREIGN PATENT DOCUMENTS

EP    2583704    4/2013
EP    2596822    5/2013

(Continued)

OTHER PUBLICATIONS

International Search Report and Written Opinion in International Application No. PCT/EP2014/071906, dated Jan. 29, 2015, 12 pages.

(Continued)

*Primary Examiner* — Rebecca E Eisenberg
(74) *Attorney, Agent, or Firm* — Fish & Richardson P.C.

(57) ABSTRACT

A medicament delivery device includes a case, a first plunger, a second plunger arranged telescopically with the first plunger, a first drive spring biasing the second plunger relative to the case, and a second drive spring biasing the first plunger relative to the second plunger.

21 Claims, 5 Drawing Sheets

(56) References Cited

U.S. PATENT DOCUMENTS

| | | | | |
|---|---|---|---|---|
| 2013/0218093 A1* | 8/2013 | Markussen | ........... | A61M 5/001 |
| | | | | 604/198 |
| 2014/0343505 A1* | 11/2014 | Henley | ............... | A61M 5/2033 |
| | | | | 604/198 |
| 2015/0080806 A1* | 3/2015 | Pribitkin | ............. | A61M 5/2033 |
| | | | | 604/189 |
| 2015/0080809 A1* | 3/2015 | Dasbach | ........... | A61M 5/31555 |
| | | | | 604/198 |

FOREIGN PATENT DOCUMENTS

| | | |
|---|---|---|
| JP | S55-75335 | 2/2015 |
| WO | WO2009/007229 | 1/2009 |
| WO | WO2011/048422 | 4/2011 |
| WO | WO 2013/005764 | 1/2013 |
| WO | WO2013/028906 | 2/2013 |

OTHER PUBLICATIONS

International Preliminary Report on Patentability in International Application No. PCT/EP2014/071906, dated Apr. 19, 2016, 9 pages.
Rote Liste, "50. Hypophysen-, Hypothalamushormone, andere regulatorische Peptide u. ihre Hemmstoffe," Chapter 50, ed. 2008, 20 pages.

* cited by examiner

MEDICAMENT DELIVERY DEVICE WITH TWO DRIVE SPRINGS

CROSS-REFERENCE TO RELATED APPLICATIONS

This application is a U.S. national stage application under 35 USC § 371 of International Application No. PCT/EP2014/071906, filed on Oct. 13, 2014, which claims priority to European Patent Application No. 13189446.1, filed on Oct. 18, 2013, the entire contents of which are incorporated herein by reference.

TECHNICAL FIELD

This disclosure relates to a medicament delivery device.

BACKGROUND OF THE INVENTION

Conventional medicament delivery devices (i.e. devices capable of delivering medicaments from a medication container) typically fall into two categories—manual devices and auto-injectors.

In a manual device, a user must provide mechanical energy to drive a medicament through a needle. This is typically done by some form of button/plunger that has to be continuously pressed during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

Auto-injectors are devices which completely or partially replace activities involved in parenteral medicament delivery from manual devices. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, handshaking and the likelihood of delivering an incomplete dose are reduced. Triggering may be performed by numerous means, for example a trigger button or the action of the needle reaching its injection depth. In some devices the energy to deliver the fluid is provided by a drive mechanism.

There remains a need for an improved medicament delivery device.

SUMMARY

Certain aspects of the present invention relate to improved medicament delivery devices.

In an exemplary embodiment according to the present invention, a medicament delivery device comprises a case, a first plunger, a second plunger arranged telescopically with the first plunger, a first drive spring biasing the second plunger relative to the case, and a second drive spring biasing the first plunger relative to the second plunger.

In an exemplary embodiment, the case includes at least one compliant arm adapted to engage the second plunger. The at least one compliant arm includes a first retention boss adapted to engage a first opening in the second plunger.

In an exemplary embodiment, the medicament delivery device further comprises a trigger button slidably coupled to the case. The trigger button includes a button wall adapted to abut the second plunger. The button wall is adapted to abut the at least one compliant arm when the trigger button is in an extended button position relative to the case and the second plunger is in a proximal plunger position relative to the case. The button wall includes a second opening adapted to receive the at least one compliant arm when the trigger button is in a depressed button position relative to the case and the second plunger is in the proximal plunger position relative to the case.

In an exemplary embodiment, the second plunger includes at least one compliant plunger beam adapted to engage the first plunger. The at least one compliant plunger beam includes a second retention boss adapted to engage a retention surface on the first plunger. The at least one compliant plunger beam abuts the case and the first plunger when the second plunger is in a proximal plunger position relative to the case. The at least one compliant plunger beam disengages the case and the first plunger when the second plunger is in a distal plunger position relative to the case. The at least one compliant plunger beam abuts a distal end of a sleeve in the case when the second plunger is in a distal plunger position relative to the case.

In an exemplary embodiment, the medicament delivery device further comprises a needle shroud coupled to the case. The needle shroud is movable between an extended shroud position and a retracted shroud position relative to the case.

In an exemplary embodiment, the medicament delivery device further comprises a medicament container disposed within the case. The medicament container is a syringe including a needle.

In some examples, drive mechanisms have one drive spring. The force of the drive spring decreases during expansion according to Hooke's law. In order to ensure, that the whole dose of medicament contained in the syringe will be completely expelled the initial force of the compressed spring must be so high that the spring force of the more expanded spring near the end of injection is still sufficiently high for pushing the plunger. The high spring force in the compressed state may result in high impact forces and pain experienced by the user which is undesirable. The decreasing spring force during expansion may result in varying injection times between medicament delivery devices of a series and in some cases in stalling of the injection before the full dose of medicament has been delivered. These disadvantages may be avoided by a medicament delivery device according to some aspects of the invention, which has at least two drive springs for driving a plunger arrangement. The medicament delivery device according to certain aspects of the invention furthermore may allow for a shorter device due to the reduced total length of the plunger arrangement.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
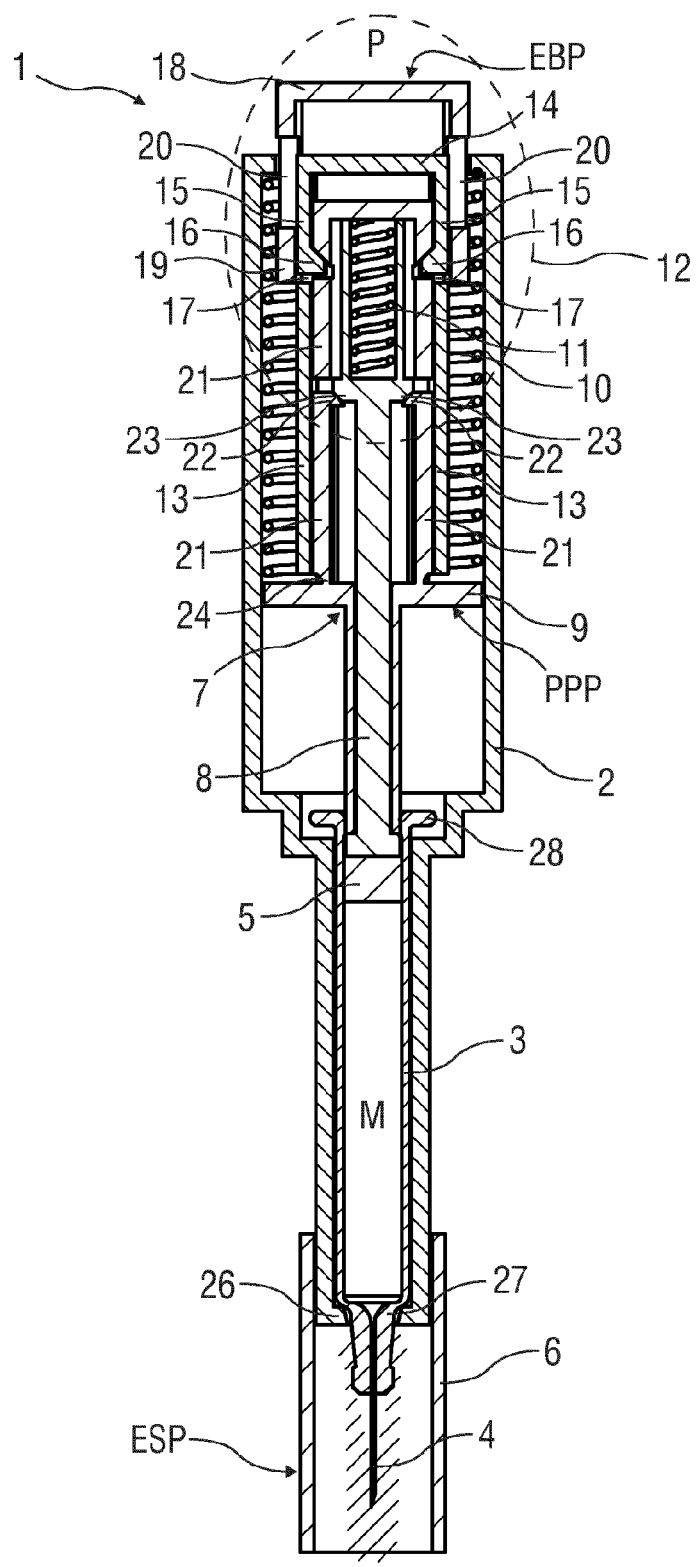
FIG. 1 is a schematic longitudinal section of an exemplary embodiment of a medicament delivery device prior to use.

FIG. 1 is a schematic longitudinal section of an exemplary embodiment of an medicament delivery device 1 prior to use. The medicament delivery device 1 comprises a case 2 adapted to receive a medicament container (e.g., a syringe 3) with a needle 4. The syringe 3 is fixed within the case 2 with respect to movement in the distal direction D, for example by a rib 26 supporting the syringe 3 at a distal end 27. Alternatively, the syringe 3 could be supported at a finger flange 28. A stopper 5 is arranged to seal a proximal end of the syringe 3 and to displace a liquid medicament M from the syringe 3 through the needle 4 when being moved in a distal direction D within the syringe 3. A needle shroud 6 is telescoped with the case 2, axially movable relative the case 2 between an extended shroud position ESP, in which the needle 4 is covered and a retracted shroud position RSP in which the needle 4 is exposed. A detent or a spring (not illustrated) may be arranged to bias the needle shroud 6 in the extended shroud position ESP.

A drive mechanism 7 is arranged to act on the stopper 5 for displacing it within the syringe 3. In an exemplary embodiment, the drive mechanism 7 comprises a first plunger 8 telescoped with a second plunger 9. In the exemplary embodiment shown in FIG. 1, the first plunger 8 is telescoped within the second plunger 9. A first drive spring 10 (e.g., a compression spring) is arranged within the case 2, proximally grounded in the case 2 and distally bearing against the second plunger 9, biasing the second plunger 9 in the distal direction D relative to the case 2. A second drive spring 11 (e.g., a compression spring) is arranged, in the exemplary embodiment, within the second plunger 9, proximally grounded in the second plunger 9 and distally bearing against the first plunger 8, biasing the first plunger 8 in the distal direction D with respect to the second plunger 9 against the stopper 5.

A plunger release mechanism 12 is arranged for selectively preventing and allowing release of the first plunger 8 and second plunger 9 for performing an injection. In an exemplary embodiment, the plunger release mechanism 12 comprises a sleeve 13 protruding distally from a proximal end wall 14 of the case 2 into the case 2. The second plunger 9 is adapted to be telescoped within the sleeve 13. In an exemplary embodiment, one or more spline/groove combinations may be formed on the second plunger 9 and the sleeve 13 to prevent rotation of the second plunger 9 relative to the sleeve 13.

In an exemplary embodiment, the sleeve 13 includes at least one compliant first arm 15 having a retention boss 16 adapted to engage a first opening 17 in the second plunger 9. In an exemplary embodiment, the first arm 15 is radially deflectable and biased radially outward. In an exemplary embodiment, at least one of the first retention boss 16 and the first opening 17 may be ramped for radially outwardly deflecting the first retention boss 16 due to the force of the first drive spring 10.

In an exemplary embodiment, a trigger button 18 is slidably arranged relative the case 2 and arranged on the proximal end wall 14. Button walls 19 protrude from a proximal surface of the trigger button 18 through the proximal end wall 14 into the case 2. The button walls 19 are arranged to outwardly support the first retention bosses 16 when the trigger button 18 is in an extended button position EBP. When the trigger button 18 is depressed and moved in the distal direction D into a depressed button position DBP a second opening 20 in the button wall 19 is axially aligned with the first retention boss 16 thus allowing radial outward deflection thereof.

Furthermore, in an exemplary embodiment, the second plunger 9 includes at least one compliant plunger beam 21 with a second retention boss 22 adapted to protrude from the second plunger 9 in a proximal direction P inwardly of the sleeve 13 and deflectable and biased in a radially outward direction. The second retention boss 22 is adapted to engage a retention surface 23 on the first plunger 8. In an exemplary embodiment, at least one of the second retention boss 22 and the retention surface 23 may be ramped for radially outwardly deflecting the second retention boss 22 due to the force of the second drive spring 11. The sleeve 13 is arranged to outwardly support the second retention bosses 22 when the second plunger 9 is in a proximal plunger position PPP such that the second retention boss 22 cannot disengage the retention surface 23. When the second plunger 9 is moved in the distal direction D into a distal plunger position DPP, the second retention boss 22 moves distally beyond an end of the sleeve 13, allowing radial outward deflection of the second retention boss 22. In another exemplary embodiment, the retention surface 23 may be replaced with an opening or a recess.

In an exemplary embodiment the plunger beam 21 may be arranged on the second plunger 9 by a live hinge 24.

In the initial state prior to use as illustrated in FIG. 1 the needle shroud 6 is in the extended shroud position ESP, the trigger button 18 is in the extended button position EBP, the first retention boss 16 keeps the second plunger 9 in the proximal plunger position PPP and the second retention boss 22 is engaged to the retention surface 23 preventing release of the first plunger 8.

An exemplary sequence of operation of the medicament delivery device 1 is as follows:

The needle shroud 6 is moved in the proximal direction P into the retracted shroud position RSP thereby exposing the needle 4. This may be achieved by placing the medicament delivery device 1 against an injection site and applying sufficient force to retract the needle shroud 6. Thus the needle 4 is inserted into the injection site.

Figure 2:
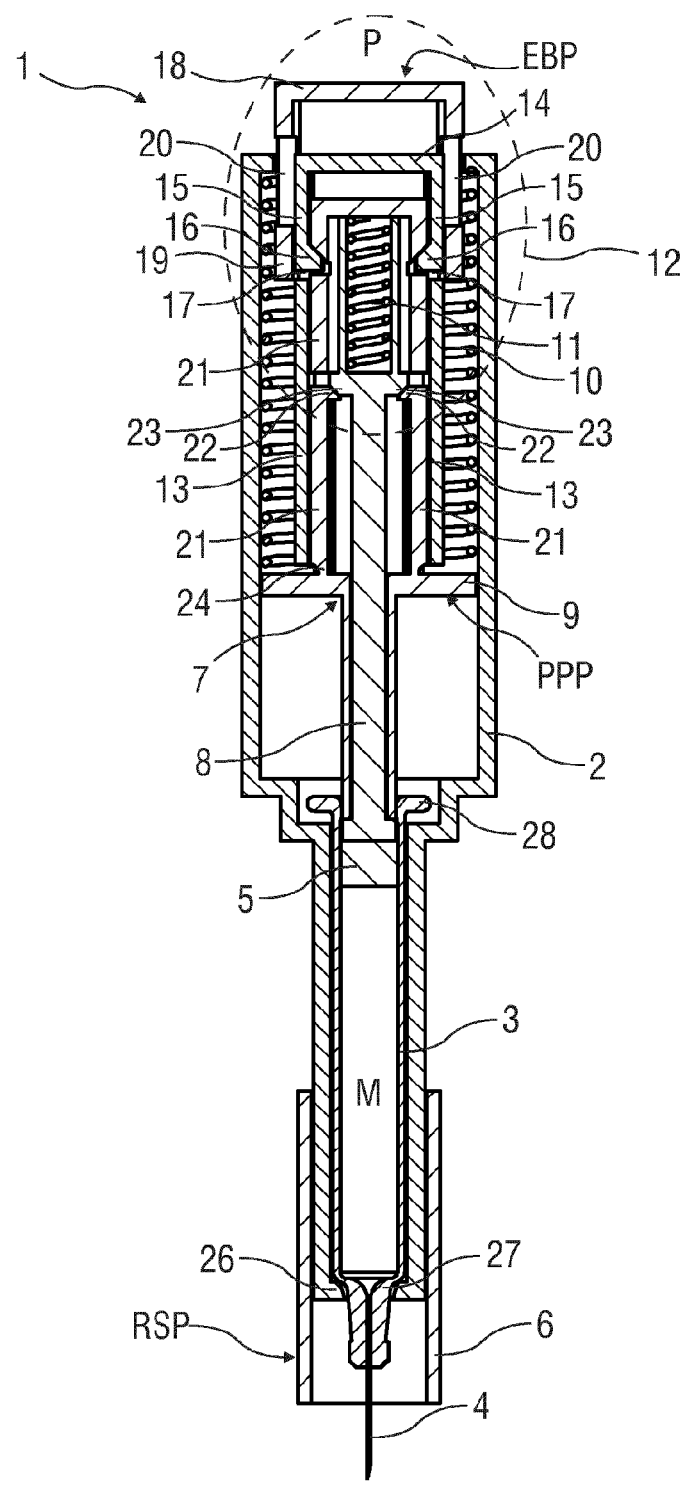
FIG. 2 is a schematic longitudinal section an exemplary embodiment of a medicament delivery device during use.

FIG. 2 is a schematic longitudinal section of the medicament delivery device 1 with the needle shroud 6 in the retracted shroud position RSP.

The user may push the trigger button 18 moving it from the extended button position EBP into the depressed button position DBP.

Figure 3:
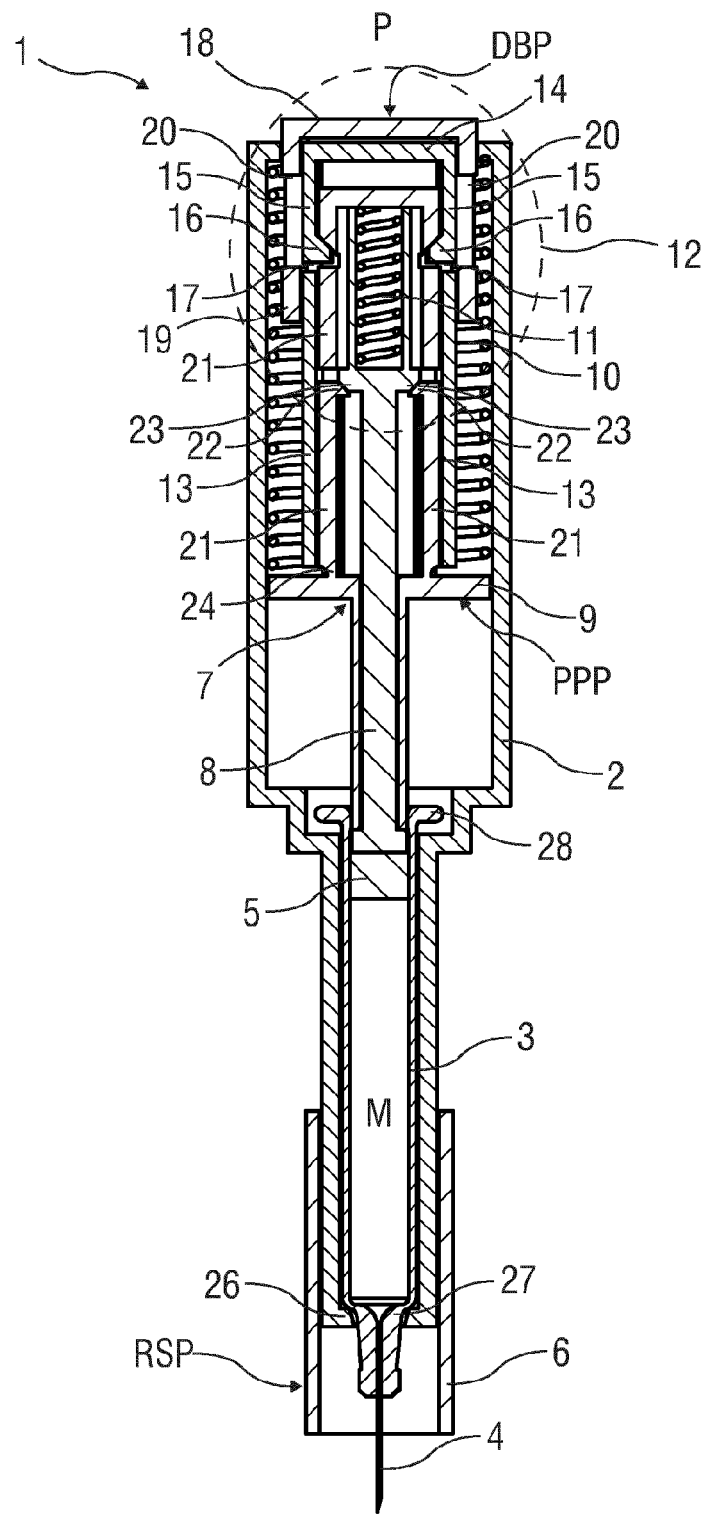
FIG. 3 is a schematic longitudinal section of an exemplary embodiment of a medicament delivery device during use.

FIG. 3 is a schematic longitudinal section of the medicament delivery device 1 with the trigger button 18 in the depressed button position DBP.

Due to depression of the trigger button 18 into the depressed button position DBP the second opening 20 in the button wall 19 is axially aligned with the first retention boss 16 thus allowing radial outward deflection of the first arm 15 thereof under force from the first drive spring 10. The second plunger 9 is thus released and moved in the distal direction D by the first drive spring 10. Due to the second drive spring 11 biasing the first plunger 8 in the distal direction D relative to the second plunger 9, the first plunger 8 moves with the second plunger 9 and in turn displaces the stopper 5 within the syringe 3 thus starting delivery of the medicament M through the injection needle 4 in a first injection stroke. The second plunger 9 continues to move until it reaches its distal plunger position DPP and abuts a stop in the case 2. When the second plunger 9 impacts the stop, a feedback (e.g., tactile and/or audible) may be provided to indicate that an injection is approximately half finished.

Figure 4:
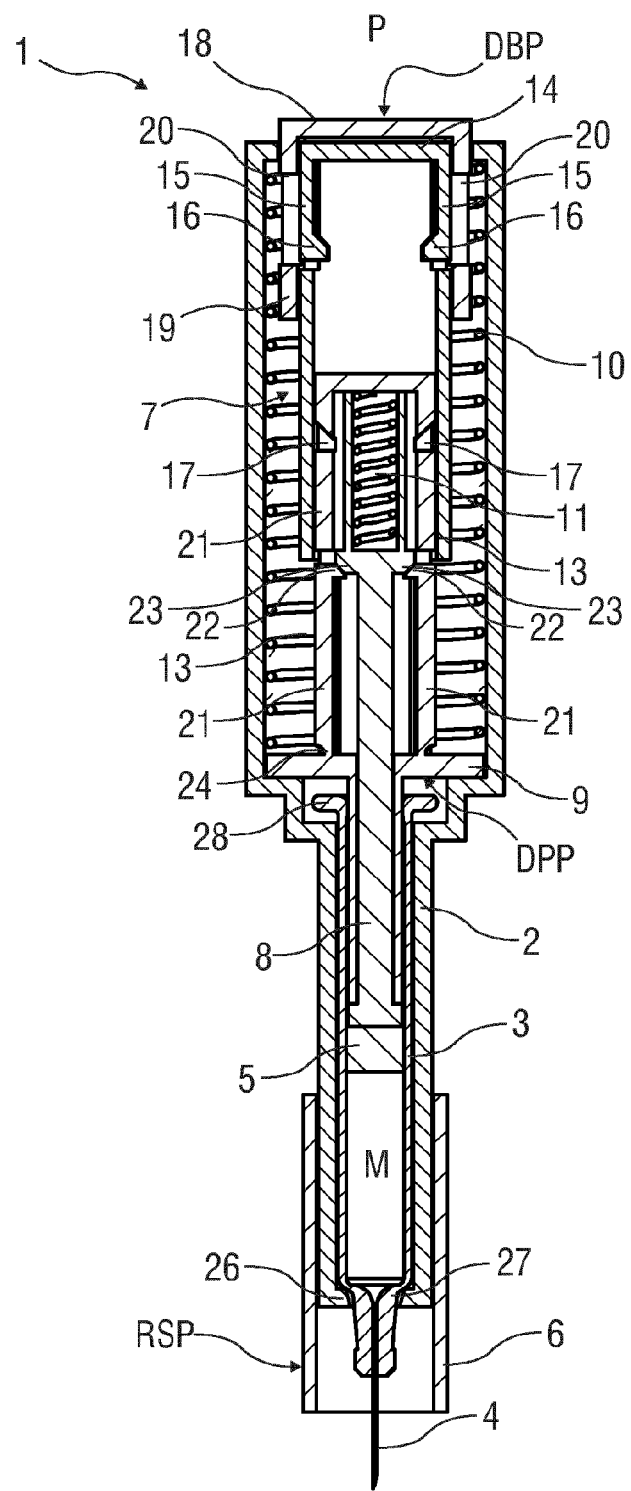
FIG. 4 is a schematic longitudinal section of an exemplary embodiment of a medicament delivery device during use.

FIG. 4 is a schematic longitudinal section of the medicament delivery device 1 at the end of the first injection stroke with the second plunger 9 in the distal plunger position DPP.

As the second plunger 9 is moved in the distal plunger position DPP, the second retention boss 22 moves distally beyond the distal end of the sleeve 13 thus allowing radial outward deflection of the second arm 21 and disengagement of the retention boss 22 and the sleeve 13 under the force of the second drive spring 11. In this position, the retention boss 22 may distally abut a proximal end of the sleeve 13. The first plunger 8 is thus released and moved in the distal direction D by the second drive spring 11 and continues displacing the stopper 5 within the syringe 3 thus completing delivery of the medicament M through the injection needle 4 in a second injection stroke. The retention surface 23 of the first plunger 8 may impact the second plunger 9 at the end of the second injection stroke to provide a second feedback (e.g., tactile and/or audible) that an injection is finished.

Figure 5:
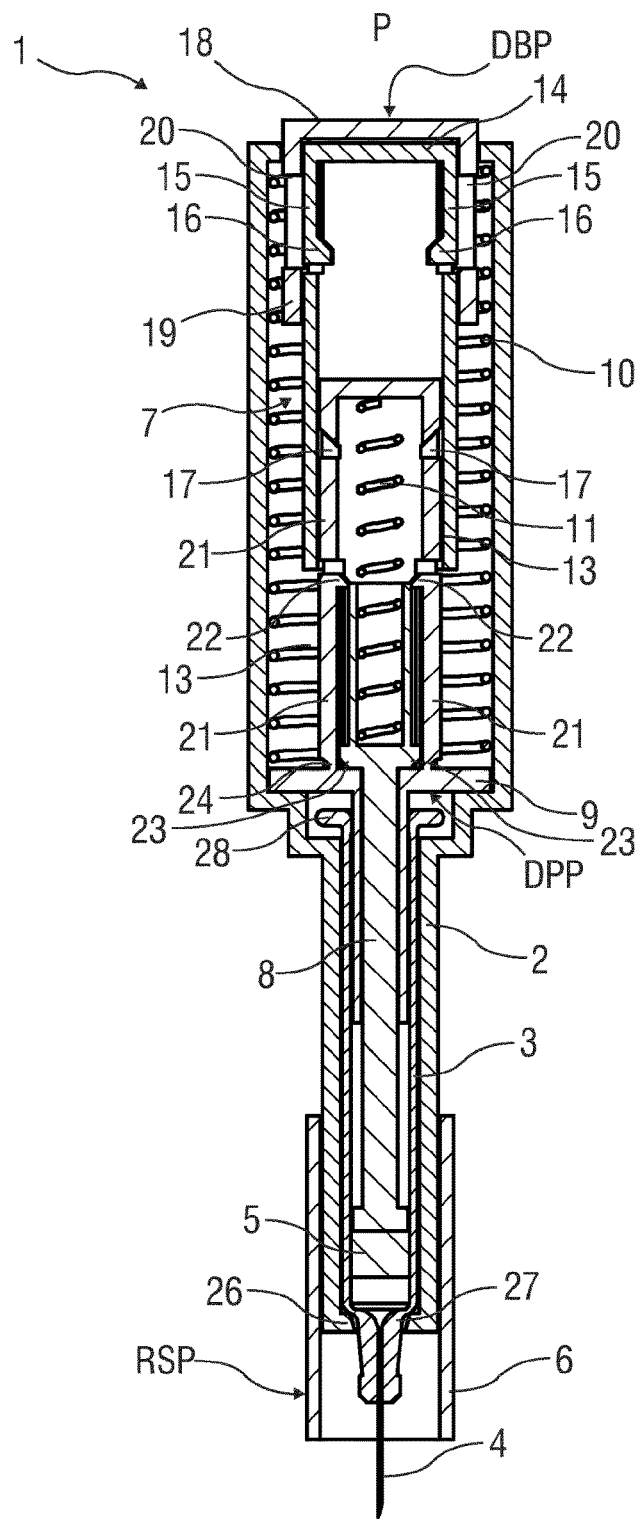
FIG. 5 is a schematic longitudinal section of an exemplary embodiment of a medicament delivery device after use.

FIG. 5 is a schematic longitudinal section of the medicament delivery device at the end of the second injection stroke.

In an alternative embodiment the second plunger 9 may be arranged to engage the stopper 5. In this embodiment the first drive spring 10 is arranged within the case 2, proximally grounded in the case 2 and distally bearing against the first plunger 8 thus biasing the first plunger 8 in the distal direction D relative the case 2. The second drive spring 11 is arranged within the second plunger 9, proximally grounded in the first plunger 8 and distally bearing against the second plunger 9 thus biasing the second plunger 9 in the distal direction D with respect to the first plunger 8 against the stopper 5.

In an alternative embodiment the drive mechanism 7 may comprise more than two plungers slidably arranged with respect to each other and biased against each other by springs. In this embodiment a respective number of retention bosses would be arranged for a phased release of the plungers.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thrombo-embolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A medicament delivery device comprising:
   a case;
   a first plunger;
   a second plunger arranged telescopically with the first plunger;
   a first drive spring configured to, in a first injection stroke, move the first plunger and the second plunger relative to the case when the first plunger and the second plunger are released; and
   a second drive spring configured to, in a second injection stroke, move the first plunger in a distal direction relative to the second plunger.

2. The medicament delivery device according to claim 1, wherein the case includes at least one compliant arm adapted to engage the second plunger.

3. The medicament delivery device according to claim 2, wherein the at least one compliant arm includes a first retention element adapted to engage a first opening in the second plunger.

4. The medicament delivery device according to claim 1, further comprising a trigger button slidably coupled to the case, the trigger button including a button wall adapted to abut the second plunger.

5. The medicament delivery device according to claim 4, wherein:
   the case includes at least one compliant arm adapted to engage the second plunger, and
   the button wall is adapted to abut the at least one compliant arm when the trigger button is in an extended button position relative to the case and the second plunger is in a proximal plunger position relative to the case.

6. The medicament delivery device according to claim 5, wherein the button wall includes a second opening adapted to receive the at least one compliant arm when the trigger button is in a depressed button position relative to the case and the second plunger is in the proximal plunger position relative to the case.

7. The medicament delivery device according to claim 1, wherein the second plunger includes at least one compliant plunger beam adapted to engage the first plunger.

8. The medicament delivery device according to claim 7, wherein the at least one compliant plunger beam includes a second retention element adapted to engage a retention surface on the first plunger.

9. The medicament delivery device according to claim 8, wherein the at least one compliant plunger beam is configured to abut the case and the first plunger when the second plunger is in a proximal plunger position relative to the case.

10. The medicament delivery device according to claim 8, wherein the at least one compliant plunger beam is configured to disengage the case and the first plunger when the second plunger is in a distal plunger position relative to the case.

11. The medicament delivery device according to claim 10, wherein the at least one compliant plunger beam is configured to abut a distal end of a sleeve in the case when the second plunger is in the distal plunger position relative to the case.

12. The medicament delivery device according to claim 1, further comprising a needle shroud coupled to the case, the needle shroud movable between an extended shroud position and a retracted shroud position relative to the case.

13. The medicament delivery device according to claim 1, further comprising a medicament container disposed within the case.

14. The medicament delivery device according to claim 13, wherein the medicament container is a syringe including a needle.

15. The medicament delivery device according to claim 13, wherein the medicament container contains at least one pharmaceutically active compound.

16. A drive mechanism for a medicament delivery device, the drive mechanism comprising:
   a plurality of plungers configured to deliver a medicament from the medicament delivery device when the plungers are released;
   a plunger release mechanism arranged relative to the plungers such that the plunger release mechanism selectively releases the plungers when the plunger release mechanism is triggered; and
   at least one retention element positioned relative to the plungers to enable a phased release of the plungers when the plunger release mechanism is triggered.

17. The drive mechanism of claim 16, further comprising a drive spring configured to bias one of the plungers in a distal direction relative to the medicament delivery device.

18. The drive mechanism of claim 17, further comprising another drive spring configured to bias another one of the plungers in the distal direction relative to the one of the plungers.

19. The drive mechanism of claim 16, wherein the plungers comprise a first plunger and a second plunger arranged telescopically with the first plunger, the second plunger being adapted to be telescoped with a sleeve of the plunger release mechanism.

20. A method of operating a medicament delivery device, the method comprising:
   inserting a needle into an injection site; and
   triggering an injection to release a plurality of plungers to cause sequential injection strokes, thereby
      delivering a first portion of medicament from the medicament delivery device through the needle during a first of the sequential injection strokes and
      delivering a second portion of the medicament from the medicament delivery device through the needle in a second of the sequential injection strokes in which a first of the plurality of plungers moves distally relative to a second of the plurality of plungers.

21. The method of claim 20, wherein triggering the injection comprises triggering a single injection such that, for each injection stroke, a corresponding drive spring drives a corresponding plunger in a distal direction to deliver a corresponding portion of the medicament.

* * * * *

UNITED STATES PATENT AND TRADEMARK OFFICE
CERTIFICATE OF CORRECTION

PATENT NO. : 10,173,012 B2  
APPLICATION NO. : 15/026680  
DATED : January 8, 2019  
INVENTOR(S) : Uwe Dasbach Page 1 of 1

It is certified that error appears in the above-identified patent and that said Letters Patent is hereby corrected as shown below:

On the Title Page

Below "Aug. 25, 2016" insert item [30], -- Foreign Application Priority Data Oct. 18, 2013 (EP) 13189446.1 --.

Signed and Sealed this
Twentieth Day of August, 2019

Andrei Iancu
*Director of the United States Patent and Trademark Office*